United States Patent [19]
Hammond et al.

[11] Patent Number: 5,880,090
[45] Date of Patent: Mar. 9, 1999

[54] TREATMENT OF VASCULAR GRAFT IMPLANTS WITH G-CSF

[75] Inventors: William P. Hammond, Redmond; Qun Shi, Seattle; Moses Hong-De Wu, Seattle; Errol S. Wijelath, Seattle, all of Wash.

[73] Assignee: The Hope Heart Institute, Seattle, Wash.

[21] Appl. No.: 933,648

[22] Filed: Sep. 19, 1997

[51] Int. Cl.$^6$ ..................................................... A61K 38/18
[52] U.S. Cl. .................................................. 514/2; 514/21
[58] Field of Search ........................................... 514/2, 21

[56] References Cited

PUBLICATIONS

Sauvage, L.R., in Haimovici et al., eds., *Haimovici's Vasular Surgery*, 4th ed., 1996.
Wu et al., *J. Vasc. Surg.* 21:862–867, 1995.
Scott et al., *J. Vasc. Surg.* 19:585–593, 1994.
Shi et al., *J. Vasc. Surg.* 25:736–742, 1997.
Clowes et al., *Am. J. Pathol.* 123:220–230, 1986.
Wu et al., *Ann. Vasc. Surg.* 10:11–15, 1996.
Shi et al., *J. Vasc. Surg.* 20:546–555, 1994.
Frazier et al. *Tex. Heart Inst. J.* 20:78–82, 1993.
Hammond et al., *Blood* 88 (suppl. 1):511a (abstract, 1996).
Asahara et al., *Science* 275:965–967, 1997.
Percivalle et al. *J. Clin. Invest.* 92:663–670, 1993.
George et al. *Thrombosis Haemostasis* 67:147–153, 1992.
Onuki et al. *Ann. Vasc. Surg.* 11:141–148, 1997.
Herring et al. *Surgery* 84:498–504, 1978.
Anderson et al., *Surgery* 101:577–586, 1987.
Kadletz et al., *J. Thorac. Cardiovasc. Surg.* 104:736–742, 1992.
Mazzucotelli et al., *Artif. Organs* 17:787–790, 1993.
Noishiki et al., *Artif. Organs* 19:17–26, 1995.
Noishiki et al., *Nat. Med.* 2:90–93, 1996.
Tong et al., *Exptl. Hematol.* 22:1016–1024, 1994.
de Revel et al., *Blood* 83:3795–3799, 1994.
Schots et al., *Bone Marrow Transplantation* 17:509–515, 1996.
Detmar et al., *J. Invest. Derm.* 98:147–153, 1992.
Bussolino et al., *J. Biol. Chem.*, 264:18284–87, 1989.
Bocchieto et al., *J. Cell. Physiol.* 155:89–95, 1993.
Flamme et al., *Development* 116:435–439, 1992.
Takehara et al., *Cell* 49:415–422, 1987.
Suri et al., *Cell* 87:1171–1180, 1996.
Harada et al., *Canc. Chemother. Pharmacol.* 38 (suppl):S115–S119, 1996.
Sauvage et al. *Arch. Surg.* 109:698–705, 1974.
Mathisen et al., *J. Vasc. Surg.* 4:33–41, 1986.
Goff et al., *J. Vasc. Surg.* 7:119–29, 1988.
Wu et al., *Ann. Vasc. Surg.* 7:156–68, 1993.
Sandmaier et al., *Blood* 87:3508–3513, 1996.

*Primary Examiner*—Jean C. Witz
*Attorney, Agent, or Firm*—Christensen O'Connor Johnson & Kindness PLLC

[57] ABSTRACT

This invention provides methods for enhancing the endothelialization of synthetic vascular grafts by administering to a graft recipient an agent that mobilizes bone marrow-derived CD34$^+$ cells into the bloodstream, that enhances the adherence to graft surfaces of blood-borne endothelial progenitors, or that stimulates the multiplication of endothelial progenitors that have adhered to the graft surfaces.

16 Claims, No Drawings

TREATMENT OF VASCULAR GRAFT IMPLANTS WITH G-CSF

FIELD OF THE INVENTION

This invention pertains to methods for enhancing the endothelialization of synthetic vascular grafts by administering an agent that is capable of mobilizing circulating endothelial cell precursors, promoting the localization of circulating endothelial precursors onto graft surfaces, or stimulating the multiplication of endothelial precursors adhered to graft surfaces.

BACKGROUND OF THE INVENTION

The surfaces of synthetic vascular prostheses are capable of provoking platelet activation and blood coagulation, generating clots that can rapidly occlude the engrafted prosthetic. Thus, the field of synthetic vascular grafts has developed at a cautious pace, and efforts to ensure their safety have included the testing of different graft materials (for review, see Sauvage, L. R., in Haimovici et al., eds., *Haimovici's Vascular Surgery*, 4th ed., 1996), and the inclusion of anti-thrombogenic materials in the pre-treatment used to seal the interstices of the graft to prevent blood loss from the vessel (Ibid.). Today, only polyethylene terephthalate (DACRON®) and polytetrafluoroethylene (TEFLON®) are approved by the Federal Drug Administration for this use. Even so, autologous grafts still are considered superior to synthetic ones because their endothelial linings, which secrete a number of natural anti-thrombotic substances, provide a far better flow surface than the material used for today's synthetic prostheses. Unfortunately, only a limited number of the body's blood vessels provide tissue suitable for use in autologous vascular transplants, and improvements in the field of synthetic prostheses would prove a boon to many patients, especially those requiring multiple heart bypasses.

Another limitation of synthetic vascular prostheses currently approved for use is that the caliber, i.e., inner diameter, of grafts deemed as acceptable must be at least 6 mm. It is believed, in fact, that no satisfactory synthetic prosthesis having a caliber below 6 mm exists today (e.g., Sauvage, 1996). Thus, the need for smaller caliber grafts remains unfulfilled, even though numerous patients require repeat coronary bypass, or have peripheral arterial occlusions below the knee or in the cerebrovascular tree, which would use small caliber synthetic grafts if these were available.

In recent years, a number of investigators have reported the occasional appearance of patches of endothelial cells growing on the walls of synthetic vascular grafts (e.g., Wu et al., *J Vasc. Surg.* 21:862–867, 1995; Scott et al., *J Vasc. Surg.* 19:585–593, 1994; Shi et al., *J Vasc. Surg.* 25:736–742, 1997). Several studies have suggested that this graft surface endothelialization originates primarily from transmural microvessels, i.e., tiny blood vessels that infiltrate the graft wall, and that originate themselves from pre-existing blood vessels (e.g., Clowes et al., *Am. J Pathol.* 123:220–230, 1986; Wu et al., *Ann. Vasc. Surg.* 10:11–15, 1996). However, other studies have indicated that at least some of the endothelialization observed in internal segments of synthetic vascular grafts appears to originate from blood-borne cells that became attached to the vessel walls (Scott et al., *J Vasc. Surg.* 19:585–593, 1994; Shi et al., *J Vasc. Surg.* 20:546–555, 1994; Wu et al. *J Vasc. Surg.* 21:862–867, 1995; Shi et al. *J Vasc. Surg.* 25:736–42, 1997; Frazier et al. *Tex. Heart Inst. J* 20:78–82, 1993; Hammond et al., *Blood* 88 (suppl. 1):511a (abstract, 1996)). This phenomenon is called "fallout endothelialization." More specifically, it has been proposed that the circulating cells that give rise to endothelial coatings of vascular prostheses may arise from the bone marrow (Hammond et al. 1996).

Indeed, circulating endothelial cells have been observed by many investigators (Asahara et al., *Science* 275:965–967, 1997; Percivalle et al. *J Clin. Invest.* 92:663–670, 1993; George et al. *Thrombosis Haemostasis* 67:147–153, 1992). The latter two of these provide evidence that circulating endothelial cells originate from the walls of blood vessels (George et al., 1992; Percivalle et al., 1993), and the study of Asahara et al. (1997) provides evidence for a circulating endothelial progenitor cell that expresses CD34, an antigen also associated hematopoietic progenitor cells, and that can participate in angiogenesis in ischemic tissues. Whatever their source, graft recipients clearly would benefit from the development of treatments promoting the deposition and outgrowth of circulating endothelial cells on the inner walls of synthetic vascular grafts.

In view of the superior anti-thrombotic properties of endothelial flow surfaces, various experimental approaches have been devised for increasing the rate of endothelialization of synthetic grafts. These include wrapping graft implants with resected segments of autologous veins (Onuki et al. *Ann. Vasc. Surg.* 11:141–148, 1997), or seeding prior to implant with autogenous endothelium, cultured endothelium or bone marrow cells (Herring et al. *Surgery* 84:498–504, 1978; Anderson et al., *Surgery* 101:577–586, 1987; Kadletz et al., *J Thorac. Cardiovasc. Surg.* 104:736–742, 1992; Mazzucotelli et al., *Artif Organs* 17:787–790, 1993; Noishiki et al., *Artif. Organs* 19:17–26, 1995; Noishiki et al., *Nat. Med.* 2:90–93, 1996; Onuki et al. *Ann. Vasc. Surg.* 11:141–148, 1997). None of these, however, has provided a practical alternative to presently used procedures.

SUMMARY OF THE INVENTION

This invention provides methods for enhancing the endothelialization of synthetic prosthetic vascular grafts. In one embodiment of the invention, an agent is administered to the graft recipient that results in increased numbers of circulating bone marrow-derived endothelial precursors or progenitors. The endothelialization-promoting agent also may enhance the adherence of circulating endothelial precursors to graft surfaces, or may stimulate the multiplication of blood-borne endothelial precursors that have become adhered to graft surfaces. Cytokines such as G-CSF and GM-CSF are useful for the subject methods.

DETAILED DESCRIPTION OF THE PREFERRED EMBODIMENT

The subject invention provides a method for promoting endothelialization in a synthetic vascular graft. In this method, an agent capable of increasing the concentration in a graft recipient of bone marrow-derived endothelial cell progenitors is administered in an amount sufficient to increase the concentration of circulating endothelial progenitors, resulting in accelerated graft healing and a reduced likelihood of thrombus formation. This agent (referred to herein as mobilizing agent or endothelialization-promoting agent) may promote endothelialization by means of inducing an increased number of circulating $CD34^+$ cells, by enhancing the adherence of circulating endothelial progenitors to graft surfaces, or by stimulating the multiplication of endothelial progenitors that have adhered to graft surfaces.

As used here, the term "endothelial cell progenitor" refers to a non-adherent cell present in the blood that expresses the CD34 antigen on its surface, and that is capable of differentiating into an adherent endothelial cell. Amounts of the agent sufficient to promote endothelialization can be determined by comparing before and after administration of the agent the levels in the patient's blood of a cell type whose level is known to increase in response to the cytokine-mediated mobilization of bone marrow. Examples of such cells include peripheral blood mononuclear cells (PBMCs) and cells that express the CD34 antigen ($CD34^+$ cells).

CD34 is a mucin-like cell surface glycoprotein of unknown function that is expressed by hematopoietic progenitors and by virtually all vascular endothelial cells of the embryo and adult. Protocols for increasing the levels of blood-borne $CD34^+$ cells have been developed in the context of efforts to overcome the damage to the hematopoietic system resulting from chemotherapy in cancer patients. These cancer patients may be treated after chemotherapy with cytokines that stimulate expansion of $CD34^+$ cells (e.g., G-CSF, GM-CSF, SCF, IL-6, etc.). Alternatively, the patients are treated prior to chemotherapy with one or more cytokines to increase the numbers of circulating $CD34^+$ cells, $CD34^+$ cells are collected from the patient's peripheral blood, stored, and then returned to the patient's circulation after chemotherapy to restore the patient's bone marrow to its original cell-generating capacity.

It has been demonstrated that $CD34^+$ or $Flk-1^+$ cell populations (Flk-1 is an endothelial cell marker) derived from peripheral blood include a subset of cells that are capable in culture of differentiating into endothelial-like cells (e.g., Asahara et al., 1997). Asahara et al. proposed that these circulating $CD34^+$ or $Flk-1^+$ cells participate in the repair of ischemic tissue. It is disclosed herein that agents capable of increasing the level of blood-borne $CD34^+$ cells can enhance the endothelialization of synthetic vascular grafts.

Agents known to be capable of mobilizing increased numbers of bone marrow-derived circulating $CD34^+$ cells include, for example, agents or combinations of agents used to mobilize $CD34^+$ hematopoietic progenitor cells in cancer patients who are receiving chemotherapy. Representative agents useful in the method of the invention include, for example, granulocyte-colony stimulating factor (G-CSF), granulocyte-macrophage-colony stimulating factor (GM-CSF), stem cell factor (SCF), and interleukin-3 (Tong et al., *Exptl. Hematol.* 22:1016–1024, 1994; de Revel et al., *Blood* 83:3795–3799, 1994; Schots et al., *Bone Marrow Transplantation* 17:509–515, 1996). Reports that GM-CSF and G-CSF can stimulate the proliferation of cultured vascular endothelial cells (Detmar et al., *J. Invest. Derm.* 98:147–153, 1992; Bussolino et al., *J Biol. Chem.,* 264:18284–87, 1989; Bocchietto et al., *J Cell. Physiol.* 155:89–95, 1993) further support the concept of systemic administration of these cytokines to promote graft endothelialization.

In one of the preferred embodiments of this invention, the endothelialization-promoting agent is G-CSF. In other preferred embodiments, enhanced endothelialization of vascular grafts is accomplished by administering other agents known to mobilize hematopoietic precursors or agents known to promote the differentiation of embryonic endothelial cell precursors, i.e., the fibroblast growth factors (Flamme et al., Development 116:435–439, 1992), as well as agents believed to induce angiogenesis, e.g., vascular endothelial growth factor and angiopoietin (Takehara et al., *Cell* 49:415–422, 1987; Suri et al., *Cell* 87:1171–1180, 1996).

The synthetic grafts of the subject invention may be composed of any material suitable for this purpose. To be suitable, a graft must be suturable to the host vessel, durable, and impervious to blood loss at implantation. Typically, synthetic grafts are pretreated prior to implantation, e.g., preclotted with autologous blood, or are coated with partially hydrolyzed proteins during manufacture. Preferred materials for the vascular grafts used in accord with the subject methods include polyethylene terephthalate and polytetrafluoroethylene (PTFE). In a particularly preferred embodiment, the synthetic vascular graft is composed of polyethylene terephthalate, which may be knit or woven. It is within the contemplation of this invention that these or other synthetic substances can be chemically modified to enhance their susceptibility to colonization by circulating endothelial precursor cells.

Using the subject method, synthetic grafts may be employed whose inner diameters are smaller than those presently regarded as safe. Representative synthetic vascular grafts useful in the practice of the invention may be from about 2 to about 9 mm, and preferably are from about 3 to about 8 mm in internal diameter. In one especially preferred embodiment, the graft is from about 3 to about 5 mm in internal diameter.

The dose and route of administration of the endothelialization-promoting agent may vary. In one representative example, when the agent is G-CSF, daily administration of from about 5 to 15 $\mu$g per kg of body weight for a total of 3 to 5 days generally will be effective to induce elevated levels of circulating $CD34^+$ cells (Harada et al., *Canc. Chemother. Pharmacol.* 38 (suppl):S115–S119, 1996; Schots et al., *Bone Marrow Transpl.* 17:509–515, 1996). Moreover, more than one endothelialization-promoting agent may be administered concomitantly. Administration of the agent may be by any conventional means, for example, intravenously or subcutaneously. In one embodiment of the invention, the endothelialization-promoting agent is administered once daily for one to fourteen days. The first dose may be administered as much as seven days prior to implantation of the graft, or may begin on the same day as graft implantation. In an alternative embodiment, the agent is administered to the intended graft recipient for several days prior to graft implantation, then the $CD34^+$ cells are collected by apheresis from the patient's peripheral blood, stored until the day of the surgery, and then returned to the patient's blood stream. The term "apheresis" refers to any procedure in which the patient's blood is subjected under sterile conditions outside the patient's body in which a subpopulation of cells is removed from the blood, then the blood returned to the patient. The subpopulation of cells is maintained in a viable condition, and may be returned to the patient at a later time. In addition, the agent preferably is administered for several days post-surgery in apheresis patients. If necessary, a compatible donor rather than the graft recipient may be treated with the agent and subjected to apheresis to collect $CD34^+$ cells, and these transplanted to the patient around the time of surgery. Suitable methods for using apheresis to collect $CD34^+$ cells from peripheral blood are known in the art, e.g., Tong et al., *Exptl. Hematol.* 22:1016–1024, 1994; Schots et al., *Bone Marrow* 17; 509–515, 1996. In another variation of the invention, $CD34^+$ cells are mobilized in the patient's blood by administering cytokines, collected by apheresis, and used to seed the walls of the vascular graft prior to its implantation. The seeded graft may be implanted immediately after seeding, or may be first cultured with suitable medium to promote attachment and growth of the endothelial progenitor cells prior to surgery.

EXAMPLES

Example 1

Bone Marrow Derived Cells Can Seed Endothelialization of Vascular Grafts

Investigations were conducted in dogs to determine whether accelerated endothelialization could be achieved by using autologous bone marrow blood (BMB) to seed vascular grafts prior to their implantation. For determining improvements in vascular surgical techniques, dogs are the experimental model of choice, and results obtained with dogs generally indicate the best outcome that can be expected in human patients (Sauvage et al. *Arch. Surg.* 109:698–705, 1974; Sauvage, L. R., 1996).

Aspirated BMB contains hematopoietic progenitor cells, stromal cells, and microvascular endothelial cells that line the bone marrow sinusoids. The experiments described here tested the hypothesis that when introduced into the graft wall by preclotting, endothelial progenitors present in BMB can proliferate or differentiate to produce a layer of endothelial cells.

Experimental Methods:

This series of experiments included two groups of subjects. The first group of subjects received grafts having dimensions of 8 mm×6 cm implanted in the descending thoracic aorta (DTA), while the second study group received 4 mm×6 cm grafts implanted into the carotid artery.

The DTA group consisted of 20 animals, twelve of which received grafts preclotted and seeded with BMB, and eight of which received grafts preclotted with peripheral blood (controls). After two and four weeks, five test animals and four control animals were sacrificed, and the remaining two test animals were sacrificed at three months.

The second group of subjects consisted of ten animals which were either preclotted and seeded with BMB, or preclotted with peripheral blood. For this group, BMB and control grafts were implanted bilaterally in carotid positions in the same dogs. The side in which each graft type was implanted was alternated between cases. Five dogs were studied after one week and five after four weeks.

The dogs used in this study weighed an average of 22.4±2.2 kG. Anesthesia was induced with 5–10 ml of 5% pentothal administered intravenously and maintained with a combination of 0.5–1% halothane and a mixture of nitrous oxide and oxygen in a 2:1 ratio via an endotracheal tube connected to a closed circuit ventilator. Crimped 8 mm and noncrimped 4 nun knitted DACRON bioknit grafts (Bard Vascular Systems Division, C. R. Bard, Inc., Billerica, Mass.) were used for the descending thoracic artery and carotid groups, respectively. In both groups, postsurgery graft flow rate was measured with a transponic flow meter (model T-208, Transonic System, Inc., Ithaca, N.Y.).

For bone marrow seeding, BMB was aspirated from the humerus diaphysis with a 15G bone marrow aspiration needle (Baxter Health Care Corporation, Deerfield, Ill.). About 15 ml of bone marrow blood was used for each step in a four-step seeding/preclot for the 8 mm grafts and about 8 ml per step for the 4 mm grafts. The pre-clotting procedure, based on that of Yates et al. (*Ann. Surg.* 188:611–622, 1878), involved pressurizing the graft with BMB until the blood clots, then repeating this procedure for a total of three times. For the fourth step, the grafts were pressurized with heparinized BMB, and soaked in heparinized BMB for a short time. After each pressurization step, excessive clots in the graft lumen were removed by a balloon catheterization. The control grafts were preclotted in the same way, but with peripheral blood drawn from the jugular vein. To evaluate the presence of $CD34^+$ cells, samples of preimplant grafts pre-clotted with either BMB or peripheral blood were fixed with HISTOCHOICE MB (Midwest Scientific, St. Louis, Mo.), embedded in wax, sectioned and stained with canine CD34 polyclonal antibodies (supplied by the Fred Hutchison Cancer Research Center, Seattle, Wash.).

For DTA implants, dogs were placed in a right lateral position, and after a left thoracotomy was made via the seventh intercostal space, approximately 8–10 cm of the upper and middle portions of the dorsal thoracic artery were dissected, with ligation of the upper five pairs of intercostal arteries. Clamps were applied, and a 5 cm-long section of the artery was excised. An 8 mm×6 cm BMB or control graft was then implanted with end-to-end anastomoses using 6-O Prolene as a running suture. The average aortic cross clamping time was about 16 minutes. When complete hemostasis was achieved, the parietal pleura was approximated over the graft and the wound was closed.

For the carotid group, because small caliber grafts were used (4 mm), platelet aggregability of the dogs was evaluated preoperatively. Only those with platelet aggregation scores of less than 30 after aspirin administration were used, and 162 mg/day of aspirin was given starting the day before surgery and continuing throughout the study period. For this surgery, the dog was placed in a supine position, and through a midline neck incision, the middle section of each carotid artery (approximately 10 cm) was mobilized. During the dissection, all lymphatics were carefully ligated. Clamps were applied and a 5 cm-long section of carotid artery was excised. The prepared 4 mm×6 cm grafts were then implanted with end-to-end anastomoses, using 7-O Prolene as a running suture. After complete hemostasis was achieved, the dissected carotid sheets were sutured back to cover the grafts and the wound was closed.

For specimen retrieval and analysis, dogs were heparinized and anesthetized. The specimen with attached aorta/artery segments was then removed, gently rinsed with phosphate buffered saline solution, longitudinally opened, pinned flat, and photographed. The condition of the perigraft tissue was inspected during harvesting. Using a digital image processing system (Image-Pro Plus, V-3.10, Media Cybernetics, Silver Spring, Md.), the thrombus-free surface score (TFS) and the percentage of the thrombus-free area over the total graft surface area were measured, and the surface image was recorded with a video system.

Three sets of 4 tissue samples were then taken across the proximal anastomosis, in the middle of the graft and across the distal anastomosis, and from other areas of interest. Each set consisted of 4 adjacent blocks for scanning electron microscopy, transmission electron microscopy, routine microscopy and immunocytochemical and histochemical studies, including staining with antibodies to detect FVIII/vWF (von Willebrand factor, an endothelial cell marker) (DEKO, code No. M-616, Carpenteria, Calif.), CD34 staining for endothelial cells, α-actin staining (DEKO, code No. M-851, Carpenteria, Calif.) for smooth muscle cells, and von Kossa and Dahl's staining for calcification. The remaining specimen was stained with 0.5% $AgNO_3$ to evaluate the number of microoostia on the flow surface, the endothelial-like cell (ELC) distribution and coverage, and the ELCC percentage, which was the percentage of the total graft surface covered with ELC. The ELCC was expressed for the total surface area and the central 4 cm area, the latter excluding the ingrowth sources from the anastomotic pannus at each end. The details of these techniques have been described previously (Mathisen et al., *J Vasc. Surg.* 4:33–41, 1986; Goff et al., *J Vasc. Surg.* 7:119–29, 1988; Wu et al., Ann. Vasc. Surg. 7:156–68, 1993). Surface lining thickness was measured on the resin sections with the micrometer in the proximal anastomotic, central and distal anastomotic areas. Throughout the studies, all grafts remained patent, i.e., unoccluded with respect to blood flow. The quantitative data were expressed as arithmetical means ± standard deviations. The statistical comparison was assessed by an unpaired or paired student's t test, and a "significant difference" was defined as $p<0.05$.

Results:

In all instances, the BMB grafts achieved significantly higher degrees of surface endothelialization than the controls, and α-actin positive smooth muscle cells were present as well. These results are summarized in Tables 1 and 2. In these tables, "BMS" means "bone marrow seeding."

TABLE 1

Comparison of ELCC (%) for DTA Samples

| | 2 weeks | | 4 weeks | |
|---|---|---|---|---|
| | Central 4 cm | Total Area | Central 4 cm | Total Area |
| BMS (N = 5) | 32.6 ± 18.2 | 35.4 ± 15.6 | 95.1 ± 3.5 | 94.5 ± 3.7 |
| Control (N = 4) | 9.0 ± 7.3 | 13.2 ± 6.8 | 75.6 ± 14.3 | 78.9 ± 12.4 |
| p-value | 0.046 | 0.0340 | 0.0210 | 0.0310 |

TABLE 2

Comparison of ELCC (%) for Carotid Graft Samples

| | 1 week | | 4 weeks | |
|---|---|---|---|---|
| | Central 4 cm | Total Area | Central 4 cm | Total Area |
| BMS (N = 5) | 80 ± 13 | 82 ± 10 | 99 ± 2 | 99 ± 2 |
| Control (N = 4) | 0 | 2 ± 1 | 58 ± 30 | 68 ± 22 |
| p-value | 0.0001 | 0.0001 | 0.037 | 0.035 |

For the DTA grafts seeded with BMB, after 4 weeks nearly the whole surface was covered with ELC (see Table 1). On the control graft surfaces, the main endothelial colonization areas were limited to the anastomotic pannus of 2-week grafts, with some larger patches scattered over the surfaces at 4 weeks. Though there were more microostia on BMB than on control grafts, the differences were not statistically significant.

Also, more microvessels were found in and around the bone marrow blood grafts and on their surfaces than in controls. Most impressively, about 80% of the BMB graft flow surfaces (with around 400 microostia) was endothelialized on the one-week carotid grafts (see Table 2). There was no significant difference in thrombus-free surface scores between the bone marrow blood grafts and control grafts, indicating that BMB pretreatment did not cause an increase in thrombogenicity.

However, the BMB grafts implanted for four weeks or longer appeared stiff. Histologic studies revealed many osteocytes with microcalcification in the outer graft wall of these grafts, but not in the inner wall or intima, even at three months. In the BMB grafts implanted longer than four weeks, osteoblasts, osteocytes, and microcalcifications were found. These undesirable side effects could affect the long-term utility of such grafts, suggesting that it may be necessary to modify the protocol to eliminate these bone progenitor cells from the bone marrow blood used for preclotting grafts.

In these experiments, smooth muscle cells were noted to have participated in the rapid neointimal healing of BMB seeded grafts, with α-actin positive cells being present as early as one week. Other observations in this procedure were that the thickness of the neointima was greater in the BMB grafts than in the control grafts, and there was no excessive surface tissue in-growth on the BMB grafts. Furthermore, the three-month BMB DTA graft results suggested that there was no development of neointimal hyperplasia between four weeks and three months. It should be noted also that in these experiments, the one week carotid grafts endothelialized faster than the two week DTA grafts.

Thus, this study demonstrates that preclotting DACRON grafts with BMB produces accelerated healing. In the experiments described here, $CD34^+$ cells were detected in the BMB but not the control graft wall prior to implantation; thus, it seems likely that the endothelialization observed in the grafts arose by differentiation from bone-marrow derived $CD34^+$ cells. It should be noted further that the BMB used for seeding also contained many types of cells that are capable of releasing a variety of growth factors that may have contributed to the observed endothelialization, e.g., dendritic cells, megakaryocytes, macrophages, and lymphocytes.

Example 2

Evidence for Vasculogenesis in the Adult by Bone Marrow Derived Cells

The following studies investigated the possibility that vascular graft endothelialization originates from bone marrow derived $CD34^+$ cells.

Using dogs as a model system, in vivo studies were performed to determine the origins of the endothelial cells that line synthetic vascular grafts. These experiments employed a canine bone marrow transplantation model in which the DNA of the donor marrow cells and the host tissue cells can be distinguished using a PCR based assay (Yu et al. *Transplantation* 58:701–706, 1994). This assay, which could detect as few as 0.5% donor cells in a total of 2,000 cells, was based on the detection of polymorphisms in a $(CA)n$ repeat unit. For the bone marrow transplantation, Beagle littermate donor/recipient pairs that were DLA matched and showed no reactivity of their blood mononuclear cells in mixed leukocyte cultures were used in all experiments. Bone marrow transplantations were performed three to six months prior to graft implantation. Transplantation recipient animals were total body irradiated to 920cGy $Co^{60}$ gamma radiation, then were infused with donor marrow over four hours at $4\times10^8$ cell/kg. Blood counts were monitored until recovery to preirradiation values. Six months or more after marrow transplantation, the six dogs used for graft implantation showed only donor marrow and peripheral blood cells, as determined by standard cytogenetics and polymorphisms among dinucleotide repeat markers.

To rule out endothelialization by transmural angiogenesis and to block perigraft tissue ingrowth, the grafts used for these experiments were made impervious by coating them with silicone rubber before implantation. These implants employed specially designed 12 cm long three-component composite grafts. These had a caliber of 6 mm, and were constructed with PTFE segments at the ends of the grafts to prevent host pannus migration, and with a central DACRON segment. The inner surface of the entire 12 cm graft was silicone-coated. Grafts were implanted into the descending thoracic aorta of six beagles using the techniques described above in Example 1.

After twelve weeks, the implants were retrieved, rinsed with 5% dextrose, and stained with 0.5% silver nitrate to help identify areas of endothelial cells. DNA was analyzed from endothelial cells removed from fresh samples by scraping or by the Hautchen technique (Obaze and Wright, *J Atheroscl. Res.* 8:861–863, 1968) after silver nitrate staining. In brief, the Hautchen technique involves fixation of vessel segments with formalin, followed by stripping off of the endothelial layer with fine forceps after the fixed segments are opened and frozen. Endothelial cells identified on Hautchens taken from fresh graft samples that stained positively for vWF antigen were used as a source of DNA, and the genotype was determined by PCR. Silver nitrate staining indicated the presence of polygonal shaped endothelial cells in these samples. The endothelial monolayer was stripped from these grafts, and DNA was extracted for PCR polymorphism analysis. Only DNA alleles corresponding to the donor were detected in the PCR product. Hematoxylin and eosin (H&E) stained sections taken from an area adjacent to the Hautchen site showed a single layer of endothelial cells on the flow surface of the silicone coated graft. The surface from the silver nitrate stained graft was also scraped from areas that contained endothelial cells, and analysis of the DNA from these scrapings demonstrated only donor alleles. Thus, these data indicate that the endothelial cells that colonized the impervious DACRON® grafts originated from donor bone marrow.

Example 3
Enhanced Vascular Graft Healing in Dogs Receiving G-CSF

The following study investigated the possibility that the mobilization of CD34$^+$ cells from the bone marrow to the bloodstream would provide a larger pool of endothelial precursors for colonizing synthetic vascular graft surfaces, and thus would enhance the rate of graft endothelialization. Three-component impervious grafts similar to those described above in Example 2 were used, and these were 12 cm in length, and with a caliber of 8 mm. These grafts were preclotted and were implanted into the descending thoracic aorta of five dogs as described above in Example 1.

Beginning on the seventh day after surgical implantation of the graft, three of the five dogs received G-CSF at 5 μg/kg subcutaneously for a total of seven days. Four weeks post-surgery, the five dogs were sacrificed, and the graft segments removed, opened longitudinally and examined. The degree of surface endothelialization will be quantitatively evaluated with silver nitrate staining using the stereomicroscope. Qualitatively, the nature of these surface cells will be evaluated histologically by light microscopy with H&E staining and immunocytochemical stains, as well as by electron microscopy.

In the two dogs that received G-CSF, 80% and 35% of the graft surfaces were covered with ELC, and in the controls, 20–30%. These findings indicate that the administration of G-CSF or other agents capable of mobilizing bone marrow is a promising avenue for promoting the healing of vascular grafts.

Example 4
Graft Healing in Dogs Administered Human G-CSF

The following experiments were designed to further demonstrate the feasibility of mobilizing bone marrow-derived endothelial progenitors as a means of promoting surface endothelialization in synthetic vascular grafts. These experiments employ two study groups. In the first group, twenty dogs receive implants into their descending thoracic aorta, and a second group of twenty dogs receive implants into their carotid arteries. Grafts are preclotted as described in Example 1, using autologous blood. Surgical procedures are as described in Example 1. Ten of the dogs in each group receive injections twice a day of 5 μg/kg of G-CSF, injected subcutaneously for 14 days, beginning seven days prior to the surgery, and continuing for an additional seven days post-surgery. In each group, five each of study and control animals are sacrificed one and four weeks post-surgery.

The effect of G-CSF on the mobilization of endothelial progenitor cells is analyzed in the study group, i.e., dogs that receive G-CSF, and peripheral blood samples taken before the administration of G-CSF at the baseline, on the day of surgery, the last day of G-CSF injection, and at the end of the study. Dogs in the control groups have only one blood sample drawn on the day of surgery. Samples are analyzed by flow cytometric analysis, and white blood cells were counted in all samples. Grafts are preclotted as described in Example 1, using autogenous blood.

The degree of surface endothelialization is quantitatively evaluated with silver nitrate staining under the stereomicroscope. Qualitatively, the nature of the surface cells is examined histologically using light microscopy and H&E staining and immunocytochemical stains, and also by electron microscopy.

Example 5
Enhanced Vascular Graft Endothelialization by Autogenous Progenitor Cell Transplantation The following experiments test the efficacy of enhancing the endothelialization of synthetic vascular grafts by transplantation of autogenous progenitor cells derived from peripheral blood of a graft recipient pre-treated with cytokines capable of mobilizing CD34$^+$ cells in the blood. The practice of transplanting mobilized autogenous progenitor cells in chemotherapy patients is well established. Because of the above demonstrations that endothelial cells that colonize vascular grafts are derived from the bone marrow, and because endothelial progenitors known to exist in bone marrow share many properties with hematopoietic precursors known to be mobilized by certain cytokines, the techniques used for autogenous progenitor cell transplantation in cancer patients may prove to be advantageous in treating vascular graft recipients.

This concept is tested in dogs as follows. A total of thirty dogs are used for this study, all of which receive grafts in their dorsal thoracic aorta as described in Example 1. Ten dogs serve as controls and receive no G-CSF, another ten receive injections of G-CSF beginning seven days prior to surgery and continuing for an additional seven days post-surgery, as described in Example 4, and the remaining ten dogs on the day of implant receive about 1×10$^8$ peripheral mononuclear blood cells mobilized by G-CSF and collected by apheresis seven days prior to surgery. Canine apheresis is performed either manually (de Revel et al., *Blood* 83:3795–3799, 1994, or using automated methods (Sandmaier et al., *Blood* 87:3508–3513, 1996). Five animals in each group are sacrificed one week and four weeks post-surgery, and analyzed as described in Example 1 above.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for promoting endothelialization of a synthetic vascular graft comprising administering to a recipient of the synthetic vascular graft an agent capable of increasing the concentration in the recipient's blood of bone marrow-derived endothelial progenitors, said agent being administered in an amount sufficient to increase the concentration in the graft recipient of said endothelial progenitors.

2. The method of claim 1, wherein the agent is selected from the group consisting of stem cell factor (SCF), granulocyte-macrophage colony-stimulating factor (GM-CSF), and granulocyte colony-stimulating factor (G-CSF).

3. The method of claim 2, wherein the agent is G-CSF.

4. The method of claim 1, wherein the synthetic vascular graft is composed of polyethylene terephthalate.

5. The method of claim 1, wherein the synthetic vascular graft is from about 2 to about 9 mm in internal diameter.

6. The method of claim 5, wherein the synthetic vascular graft is from about 3 to about 5 millimeters in internal diameter.

7. The method of claim 1, wherein the agent is administered daily for 1 to 14 days.

8. The method of claim 1, wherein the agent is administered prior to or within 3–7 days after implantation of the graft.

9. The method of claim 8, wherein the agent is administered for at least 3 days prior to implantation of the graft, peripheral blood mononuclear cells are collected by apheresis prior to graft implantation, and the collected peripheral blood mononuclear cells are perfused into the graft recipient within 3 days of graft implantation.

10. A method for promoting endothelialization in a synthetic vascular graft wherein the recipient of the synthetic vascular graft is a human comprising administering to the graft recipient an amount of G-CSF sufficient to increase the concentration in the graft recipient of peripheral blood mononuclear cells or cells that express the CD34 antigen.

11. The method of claim 10, wherein the synthetic vascular graft is composed of polyethylene terephthalate.

12. The method of claim 10, wherein the synthetic vascular graft is from about 2 to about 9 millimeters in internal diameter.

13. The method of claim 12, wherein the synthetic vascular graft is from about 3 to about 5 millimeters in internal diameter.

14. The method of claim 10, wherein the G-CSF is administered daily for 1 to 14 days.

15. The method of claim 10, wherein the G-CSF is administered prior to implantation of the graft.

16. The method of claim 15, further comprising administering to the graft recipient within 3 days of graft implantation peripheral blood mononuclear cells collected by apheresis from the graft recipient after at least 3 days of G-CSF administration to the graft recipient.

* * * * *